United States Patent [19]

Foa et al.

[11] 4,351,952

[45] Sep. 28, 1982

[54] PROCESS FOR PREPARING PHENYL PYRUVIC ACIDS

[75] Inventors: Marco Foà, Novara; Alessandro Moro, Pernate; Andrea Gardano, Trino Vercellese; Luigi Cassar, Novara, all of Italy

[73] Assignee: Montedison S.p.A., Milan, Italy

[21] Appl. No.: 165,019

[22] Filed: Jul. 1, 1980

[51] Int. Cl.³ .............................................. C07C 51/10
[52] U.S. Cl. ................................ 562/406; 260/465 D
[58] Field of Search .......................... 562/406, 465 D

[56] References Cited

U.S. PATENT DOCUMENTS 4,152,352  5/1979  Perron .................................. 562/406

Primary Examiner—Paul J. Killos

[57] ABSTRACT

Phenyl pyruvic acid and substituted derivatives thereof are synthesized by catalytic carbonylation of a benzyl halide in the presence of a catalytic system based on carbonyl complexes of cobalt or precursors thereof.

11 Claims, No Drawings

PROCESS FOR PREPARING PHENYL PYRUVIC ACIDS

BACKGROUND OF THE INVENTION

The following formula (I) can be attributed to the phenyl pyruvic acids obtainable according to the present invention:

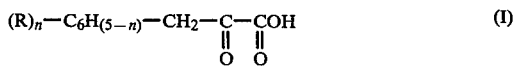  (I)

wherein n is an integer selected from 1, 2 and 3, and substituent or substituents R, like or unlike one another, are hydrogen, alkyl or alkoxy groups having 1 to 4 carbon atoms, in their turn also substituted by alkoxy groups having 1 to 4 carbon atoms, or they are halogens, nitrile groups, acyl groups, etc.

Several methods of preparing phenyl pyruvic acid have been proposed, such as the transposition of phenylglycidic acid with concentrated HCl, the hydrolysis of ethyl phenyloxalacetate, the condensation of N-diethyl-oxamic ester with benzyl-magnesium bromide, etc.

These methods, however, besides being alien to the process of the present invention, due to the complexity of the production steps involved, the uncommon starting materials and reactions required, and the yields not always profitable, have few possibilities of being actually applied to an industrial scale.

Processes have also been described for preparing phenyl pyruvic acids by carbonylation of benzyl halides, also substituted, with CO under pressure in the presence of a carbonylation catalyst, such as the salts of the hydrocarbonyl compounds of Fe, Co and Ni, the carbonyls of Fe, Ni or Co in an alcoholic-aqueous medium, and of a base consisting of oxides and/or hydroxides of alkaline earth metals.

However, in the last-mentioned processes, the phenyl pyruvic acids are obtained in the form of a mixture with the corresponding phenylacetic acids (products of mono-carbonylation) which form simultaneously in a quantitative ratio. Therefore, to direct the reaction towards the highest possible selectivity in respect to the phenyl pyruvic acids (products of di-carbonylation) to be obtained, the actual operating conditions require operation with high pressures of gaseous CO, in any case not lower than about 50-60 atm. Furthermore, under such conditions, the quantitative ratio between phenyl pyruvic acid and phenyl acetic acid or substituted derivatives thereof is not always selective enough; for example for the non-substituted compound (phenyl pyruvic acid) the selectivity does not exceed a value of 4.5. In consequence, the maximum selectivity obtainable in phenyl pyruvic acid is rather low.

THE PRESENT INVENTION

It is an object of the present invention to provide a simple and economic method of preparing phenyl pyruvic acid and substituted derivatives thereof, which is free from the drawbacks of the prior art mentioned herein, and which, in particular, due to the values of the operative parameters provided—such as temperature and pressure—and due to the high values of the conversions and selectivities rates in the desired phenyl pyruvic acid, is especially adapted to industrial applications.

This and still other objects, which will be evident to a technician skilled in the art from the following description, are achieved, according to this invention, by a process for preparing phenyl pyruvic acid and substituted derivatives thereof having formula (I) by carbonylation with gaseous CO of the corresponding benzyl halides of formula (II):

  (II)

wherein R and n have the meanings as in formula (I) and X is selected from chlorine and bromine, in the presence of carbonyl complexes of cobalt and of a basic inorganic agent, characterized in that the reaction is conducted in an aqueous-organic medium consisting of a water-mixable ether solvent, preferably selected from among dioxane, dimethoxyethane and tetrahydrofuran, at a pressure ranging approximately from 5 to 60 atm., preferably from 10 to 40 atm. approximately, and at a temperature approximately ranging from 50° to 90° C.

As compared with the prior art in general, the present invention represents an important progress as regards the carbonylation reaction. In fact, the use of water-mixable ether solvents, according to this invention, generally permits to obtain acceptable values of the selectivities in the desired phenyl pyruvic acid, under substantially milder parameter conditions.

The process can be schematically represented by the following equations:

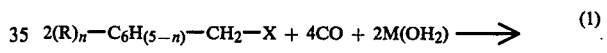  (1)

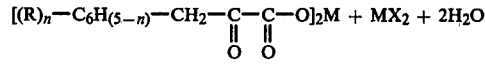

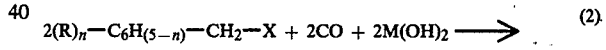  (2)

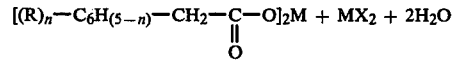

wherein R and n have the meanings specified for formula (I), X is a halide selected from chlorine and bromine and M is an alkaline earth metal, preferably selected from Ca, Mg, Ba.

Equation (1) leads to the alkaline earth salt of the phenyl pyruvic acid to be obtained, equation (2) to the corresponding phenyl acetic acid, as by-product of the process.

The free acids are easily obtained from the salts by simple shifting with strong mineral acids, extraction with solvents, etc., according to known techniques. The substratum to be carbonylated is a benzyl halide selected from chlorides and bromides, preferably chlorides, also substituted, having formula (II) as defined hereinabove.

Some examples of suitable R substituents are the halogens, chlorine or bromine, the alkyls and alkoxy groups having up to 4 carbon atoms; nitrile groups, acyl groups.

Benzyl chloride, p-methyl-benzyl chloride, para- and ortho-chloro-benzyl chloride have proved to be efficient halides.

The reaction medium consists in a mixture, with water, of an ether solvent at least partially mixable with water, as defined hereinabove.

Preferably, the organic medium is a solvent selected from among dioxane, dimethoxyethane and tetrahydrofuran in admixture with water up to a water content comprised between approximately 10% and 30% by volume.

The catalyst system is composed of a carbonyl complex of cobalt or of salts of cobalt hydrocarbonyl (cobalt-tetracarbonylates) or by precursors thereof.

Preferably, the catalyst is selected from $Co_2(CO)_8$ and the Na, Co and Fe salts of cobalt hydrocarbonyl. It is possible to use systems composed of cobalt chloride with iron in powder and sulphurated activators (sulphur and sodium thiosulphate) which, under the temperature and pressure conditions of the reaction, and in the presence of CO, yield the Fe salt of the cobalt hydrocarbonyl. Such a catalyst system is described in the literature.

Said carbonyl compounds of Co and their hydrocarbonyl salts are compounds which are available on the market or which can be prepared according to known techniques. For example, the cobalt compounds are obtained according to known techniques as follows: $Co_2(CO)_8$ is prepared from $CoCO_3$ and CO under hydrogen pressure in petroleum ether, while $Na[Co(CO)_4]$ is prepared in its turn by reduction of $Co_2(CO)_8$ with a sodium amalgam at 1% in tetrahydrofuran.

The catalyst is added either as a solid or as a solution in the solvent in an inert atmosphere (nitrogen), in a catalytic amount, advantageous results being obtained with values comprised between 0.1 and 0.001 mole of catalyst for 1 mole of benzyl halide.

The reaction is conducted, as stated, in the presence of inorganic alkaline earth bases selected from the oxides and hydrates of Ca, Mg and Ba, which are introduced in amounts ranging approximately from 1 mole to 2 moles per mole of benzyl halide.

The concentration of the benzyl halide in the reaction medium is advantageously comprised between about 10% and about 20% by weight, without being critical.

The carbon monoxide is introduced at a pressure approximately ranging from 5 to 60 atmospheres, preferably from 10 to 40 atmospheres.

The temperature is maintained approximately between 50° and 90° C. for times comprised between 5 and 10 hours, sufficient to complete the reaction.

According to a practical procedure, the process of the invention can be carried out as follows:

In a nitrogen atmosphere the catalyst, freshly and separately prepared, is added to the ether solvent (dioxane at 20% by vol. of $H_2O$) in the desired ratio. The resulting solution is then charged into an autoclave equipped with a stirrer, a temperature regulator and reagent inlet system, and is then stirred. Subsequently, always under a nitrogen head, the base is added in an at least equimolar amount in respect of the benzyl halide, and then the benzyl halide (benzyl chloride). Successively, CO is introduced in a large stoichiometric excess, at the desired temperature (about 65° C.) and pressure (about 20 atm.), under stirring for some hours until conclusion of CO absorption is observed.

At the conclusion of the CO absorption, the reaction mixture is treated according to conventional techniques in order to separate the products. For example, the reaction mixture is filtered and the solid is washed with $H_2O$ and with an organic solvent (ethyl ether). The residue so obtained is treated with an aqueous solution of HCl and extracted with an organic solvent (ethyl ether), from which, by distillation, the phenyl pyruvic acid is obtained at a purity degree higher than 95% and can be further purified.

From the filtrate, if so desired, the phenylacetic acid formed and therein contained can be recovered according to known methods. For example, the filtrate is acidified and extracted in ether. The ether extract is treated with an aqueous solution saturated with sodium bicarbonate. The acidified alkaline extract is extracted in ether so that phenyl acetic acid is obtained. The residual ether extract is evaporated and the residue consists mainly of unreacted benzyl halide, which is recycled, and so on.

The present process, due to the mild operating conditions of temperature and pressure and to the high selectivity in phenyl pyruvic acid, appears particularly advantageous for industrial applications on a large scale.

The present invention will be further described by the following examples which are given, however, for merely illustrative purposes.

Examples 8 and 9 are given to prove that water-unmixable ethers (anisole and di-isopropyl ether) do not allow the reactions leading to phenyl pyruvic acid.

EXAMPLES 1–9

Dioxane (200 cc), $H_2O$ (40 cc), $Ca(OH)_2$ (31.0 g), benzyl chloride (34.3 g) and $NaCo(CO)_4$ (1 g) were introduced, in a nitrogen atmosphere, into a 500 cc autoclave, equipped with a mechanical stirrer. After washing with CO, 20 atm. of CO were charged in cold conditions and the temperature was brought to 65° C. The reaction mixture was kept under stirring for 8 hours, by feeding CO in order to keep the pressure constant.

At the conclusion of the CO absorption, the autoclave was cooled and discharged. The crude reaction product was filtered and the solid cake was repeatedly washed with water and ethyl ether.

The residual solid was dissolved in water and hydrochloric acid and successively extracted in ether. The anhydrified ether extract was evaporated to dryness, so obtaining 33.3 g of phenyl pyruvic acid (PPA). Yield = 80% calculated on the converted benzyl chloride.

The washing water and ether then were combined with the filtrate. The whole was acidified with HCl and extracted in ether.

The ether extract was washed with a saturated solution of $NaHCO_3$. The ether extract was then anhydrified by evaporation to dryness, thus obtaining 1.9 g of residue consisting of starting benzyl chloride.

The alkaline waters were made acidic and extracted with ether. 3.8 g of phenylacetic acid (PAA) were obtained from the ether extract after evaporation. The yield was equal to 11%, calculated on the converted benzyl chloride.

A similar procedure was followed for all the examples reported in Table 1.

All the tests were carried out with 34.1 (269 m.moles) of benzyl chloride and 1.0 g (5.15 m.moles) of $NaCo(CO)_4$ or equivalent amounts of $Co_2(CO)_8$ (Example 7) or of $CoCl_2.6H_2O$ (Example 4). The precentage by volume of $H_2O$ was 16.6%. The yields were calculated on the converted halide.

TABLE 1

| Example | Solvent | P Atm. | T °C. | Conversion | Yield PPA wt. % | Yield PAA wt. % | PPA/PAA |
|---|---|---|---|---|---|---|---|
| 1 | Dioxane/$H_2O$ | 20 | 65 | 94.4 | 80 | 11 | 7.3 |
| 2 | Dioxane/$H_2O$ | 10 | 65 | 82 | 81 | 12.4 | 6.5 |
| 3 | Dioxane/$H_2O$ | 30 | 65 | 92 | 84 | 12 | 7 |
| 4 | THF/$H_2O$ | 20 | 65 | 56 | 75 | 13.5 | 5.5 |
| 5 | THF/$H_2O$ | 40 | 65 | 62 | 85 | 6.6 | 12.8 |
| 6 | THF/$H_2O$ | 55 | 77 | 90 | 77 | 14 | 5.5 |
| 7 | Dimethoxyethane/$H_2O$ | 20 | 65 | 94.4 | 79 | 14 | 5.6 |
| 8 | Anisole/$H_2O$ | 20 | 65 | — | — | — | — |
| 9 | Diisopropylether/$H_2O$ | 20 | 65 | — | — | — | — |

THF = tetrahydrofuran
PPA = phenyl pyruvic acid
PAA = phenyl acetic acid

EXAMPLES 10-12

Operation was according to the modalities and with the apparatuses described in Example 1, but using successively, as benzyl halide to be subjected to carbonylation, para-methyl-benzyl chloride (Example 10), ortho-chloro-benzyl chloride (Example 11) and para-chloro-benzyl chloride (Example 12). The yields obtained are recorded in Table 2. In these examples the yields were calculated on the benzyl halide introduced. The PPA/PAA ratios (selectivities in respect of phenyl acetic acid) were high.

TABLE 2

| Example | Benzyl Halide | PPA Yield calculated on the benzyl halide introduced |
|---|---|---|
| 10 | p-methyl-benzyl chloride | 78 |
| 11 | o-chloro-benzyl chloride | 56 |
| 12 | p-chloro-benzyl chloride | 58 |

The phenyl pyruvic acids obtained in the practice of this invention are interesting compounds having considerable possibilities as concerns various uses. In addition to being useful intermediates for the synthesis of organic compounds in general, especially of fine chemicals, they can be usefully employed especially in the preparation of compounds of high biochemical interest such as, for example, phenylalanine by reducing amination, and 2-hydroxy-3-phenyl-propionic acid by hydrogenation of the phenyl pyruvic acid, and so on.

What we claim is:

1. A process for preparing phenyl pyruvic acids having the formula (I):

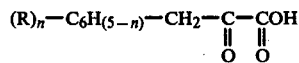

$$(R)_n\text{—}C_6H_{(5-n)}\text{—}CH_2\text{—}\underset{O}{\overset{\|}{C}}\text{—}\underset{O}{\overset{\|}{C}}OH \qquad (I)$$

in which n is an integer selected from 1, 2 and 3 and substituent or substituents R, which may be the same or different, are hydrogen, alkyls or alkoxy groups having 1 to 4 carbon atoms, alkyl or alkoxy groups substituted by alkoxy groups having 1 to 4 carbon atoms, halogens, nitrile groups, or acyl groups, by carbonylation with CO of benzyl halides having the formula (II):

$$(R)_n\text{-}C_6H_{(5-n)}\text{—}CH_2X \qquad (II)$$

wherein n and R have the same meanings as in formula (I) and X is a halogen selected from chlorine and bromine, in the presence of carbonyl complexes of cobalt and of an inorganic basic agent, characterized in that the carbonylation reaction is conducted in an aqueous-organic medium consisting of a water-mixable ether solvent, at a pressure raging from about 5 to about 60 atmospheres and at a temperature ranging from about 50° to about 90° C.

2. The process of claim 1, in which the solvent is a water-mixable ether selected from the group consisting of dioxane, dimethoxyethane and tetrahydrofuran.

3. The process of claims 1 or 2, in which the carbonylation reaction is conducted at a pressure ranging from about 10 to about 40 atmospheres.

4. The process of claim 1, characterized in that the benzyl halide is selected from the group consisting of benzyl chloride, para-methyl-benzyl chloride, para-chloro-benzyl chloride and ortho-chloro-benzyl chloride.

5. The process of claim 1, in which the ether solvent is employed in admixture with water up to a water content ranging from about 10% to about 30% by volume.

6. The process of claim 1, in which the catalyst is selected from the carbonyl complexes of cobalt and the salts of cobalt hydrocarbonyl.

7. The process of claim 6, in which the catalyst is selected from $Co(CO)_8$ and the Na, Co, Fe salts of cobalt hydrocarbonyl.

8. The process of claim 6, in which the catalyst is composed of cobalt chloride, iron in powder and sulphurated activators.

9. The process of claim 1, in which the carbonylation reaction is conducted in an inert atmosphere and in the presence of amounts of cobalt catalyst comprised between 0.1 and 0.001 mole for 1 mole of benzyl halide.

10. The process of claim 1, in which the carbonylation reaction is conducted in the presence of an inorganic basic agent selected from the oxides and hydrates of Ca, Mg and Ba, in an amount ranging from about 1 mole to about 2 moles per 1 mole of benzyl halide.

11. The process of claim 1, in which the benzyl halide concentration ranges from about 10% to about 20% by weight.

* * * * *